(12) United States Patent
Ahmad

(10) Patent No.: US 8,492,426 B1
(45) Date of Patent: Jul. 23, 2013

(54) USE OF CARVEDILOL FOR TREATMENT OF DIABETES MELLITUS

(76) Inventor: Anis Ahmad, Moline, IL (US)

( * ) Notice: Subject to any disclaimer, the term of this patent is extended or adjusted under 35 U.S.C. 154(b) by 0 days.

(21) Appl. No.: 13/547,047

(22) Filed: Jul. 12, 2012

(51) Int. Cl.
*A61K 31/40* (2006.01)

(52) U.S. Cl.
USPC ........................................ 514/411

(58) Field of Classification Search
USPC ........................................ 514/411
See application file for complete search history.

(56) References Cited

U.S. PATENT DOCUMENTS

| | | | |
|---|---|---|---|
| 4,503,067 | A | 3/1985 | Wiedemann |
| 6,699,997 | B2 | 3/2004 | Hildesheim |
| 7,056,942 | B2 | 6/2006 | Hildesheim |
| 7,126,008 | B2 | 10/2006 | Hildesheim |
| 7,268,156 | B2 | 9/2007 | Brook |
| 2005/0009897 | A1 * | 1/2005 | Anderson et al. ............ 514/411 |

OTHER PUBLICATIONS

U.S. Appl. No. 10/473,667, filed Jan. 13, 2005, Anderson.
U.S. Appl. No. 10/244,433, filed Apr. 17, 2003, Kitahara.

* cited by examiner

*Primary Examiner* — Rei-tsang Shiao
(74) *Attorney, Agent, or Firm* — UAQ Law Group, LLC; Umair A. Qadeer

(57) ABSTRACT

A method of treating diabetes by administering Carvedilol in patients and diabetes mellitus. This method of treatment will eliminate the need for insulin and other blood sugar controlling agents in hypertensive patients with Type II diabetes mellitus, and will significantly reduce the required dosage of insulin and eliminate the need for other blood controlling agents in patients with Type I diabetes mellitus. This method will also delay and/or prevent the progression of non-insulin dependent Type II diabetes mellitus to insulin-dependent Type II diabetes mellitus. Moreover, this method has been shown to preserve improve insulin receptor sensitivity such that patient's $HbA_{1c}$ level reaches and is maintained at or near 7% or less.

18 Claims, No Drawings

USE OF CARVEDILOL FOR TREATMENT OF DIABETES MELLITUS

CROSS REFERENCE TO RELATED APPLICATIONS

None.

FIELD OF INVENTION

The invention is generally directed to a method of treating diabetes mellitus by administering Carvedilol in an effective amount to patients with diabetes mellitus. More specifically, this method of treatment will eliminate the need for insulin and other blood sugar controlling agents in patients with Type II diabetes mellitus, will significantly reduce the required dosage of insulin in patients with Type I diabetes mellitus and hypertension, and will delay and/or prevent the progression of non-insulin dependent Type II diabetes mellitus to insulin-dependent Type II diabetes mellitus. This method achieves the aforementioned results by preserving insulin secretion and by improving insulin receptor sensitivity.

STATEMENT REGARDING FEDERALLY SPONSORED RESEARCH OR DEVELOPMENT

No federal funds were used to develop or create the invention disclosed and described in the patent application.

REFERENCE TO SEQUENCE LISTING, A TABLE, OR A COMPUTER PROGRAM LISTING COMPACT DISK APPENDIX

Not Applicable

BACKGROUND

Diabetes mellitus is one of the most common metabolic disorders in humans today. Nearly 26 million people, roughly 8.3% of the population, have been diagnosed with the disease in the United States alone. Type I diabetes typically appears in childhood or early adulthood. Type II diabetes, consisting of both insulin-dependent and non-insulin-dependent types, typically appears later in life as the result of improper diet, lack of exercise, or a combination thereof. Both forms of diabetes alter the body's ability to convert blood glucose into energy, leading to elevated levels of blood glucose. Chronically high levels of blood glucose may increase the risk for long-term vascular complications such as coronary disease, heart attack, stroke, heart failure, kidney failure, blindness, erectile dysfunction, neuropathy (loss of sensation, especially in the feet), gangrene, and gastroparesis (slowed emptying of the stomach). Improper blood glucose control also increases the risk of short-term complications after surgery such as poor wound healing.

Diabetes mellitus is a kind of metabolic disease that is brought about by either the insufficient production of insulin or the inability of the body to respond to the insulin formed within the system. Insulin is produced by the pancreas and is the principal hormone that regulates uptake of glucose from the blood into all tissue. The insulin receptor is a transmembrane receptor that is activated by insulin, IGF-I, and IGF-II and belongs to the large class of tyrosine kinase receptors. The main activity of activation of the insulin receptor is inducing glucose uptake. For this reason "insulin insensitivity," or a decrease in insulin receptor signaling, leads to Type II diabetes mellitus. In Type II diabetes mellitus the cells are unable to take in glucose, and the result is hyperglycemia (an increase in circulating glucose). Insulin deficiencies, the insensitivity of its receptors, or a combination of both play a central role in all forms of diabetes mellitus. Diabetes mellitus Type I is caused by the decrease of β-cells found in the islets of Langerhans in the pancreas. β-cells primarily produce insulin and accordingly, their loss will lead to large insulin deficiencies in the body. Type II diabetes mellitus is generally characterized by the body's resistance to insulin. This is primarily attributed to the loss of, or diminished function of, certain insulin receptors in the tissues that are supposed to mediate the entrance of insulin into the body's cells.

Diabetes mellitus is a chronic disease which cannot be cured. Prior to this invention, management of the disease focused on keeping blood sugar levels as close to normal ("euglycemia") as possible, without causing hypoglycemia. This could only be accomplished with diet, exercise, and use of appropriate medications (insulin in the case of Type I diabetes, and oral medications, as well as possibly insulin, in Type II diabetes).

Synthetic insulin is readily available to patients, but the high cost and inconvenience of administration drives many patients away. It is not uncommon for patients to be charged several hundred dollars per month for their insulin prescriptions. Likewise, the proper regulation of diabetes requires patients to constantly monitor their blood glucose levels throughout the day. To successfully monitor blood glucose levels patients are forced to retrieve and test small blood samples. Because monitoring the disease is so difficult and expensive, diabetes remains a serious disease responsible for many deaths. Even with the proper dosage of insulin, patients can still suffer eye damage, delayed wound healing, and other serious consequences.

The conventional methods of treating diabetes are incredibly inconvenient and costly. Thus, there remains a need for diabetes treatments.

SUMMARY OF THE INVENTION

The present invention is directed to methods of treating patients with diabetes by administering Carvedilol.

(±)-1-(Carbazol-4-yloxy-3-[[2-(o-methoxyphenoxy-)ethyl]amino]-2-propanol is known as Carvedilol. This compound is a nonselective β-adrenergic blocking agent with α-1-blocking activity, designed to treat hypertension and heart failure. Carvedilol is claimed in U.S. Pat. No. 4,503,067 (assigned to Boehringer Mannheim, GmbH, Mannheim-Waldhof, Fed. Rep. of Germany), issued Mar. 5, 1985. The processes of preparing Carvedilol and active ingredient equivalents (crystalline solids of Carvedilol), processes for the manufacture thereof, and pharmaceutical compositions thereof are claimed in U.S. Pat. Nos. 6,699,997 (assigned to Teva Pharmaceutical Industries Ltd.), issued Mar. 2, 2004; 6,710,184 (assigned to Teva Pharmaceutical Industries Ltd.), issued Mar. 23, 2004; 7,056,942 (assigned to Teva Pharmaceutical Industries Ltd.), issued Jun. 6, 2006; and 7,126,008 (assigned to Teva Pharmaceutical Industries Ltd.), issued Oct. 24, 2006. Reference should be made to said patents for full disclosure, including the methods of preparing and using this compound. The entire disclosure of each of the '067 patent; '997 patent; '184 patent; '942 patent; and '008 patent are incorporated by reference herein.

The present invention is based, in part, on the surprising discovery that Carvedilol can improve insulin receptor sensitivity. In diabetic patients, this improved insulin receptor sensitivity can help the body naturally regulate the level of blood glucose. Glycated hemoglobin ($HbA_{1c}$) is an accurate measure of a patient's average blood glucose concentration. $HbA_{1c}$ testing is the preferred method of monitoring blood sugar control in patients with diabetes mellitus. Patients with diabetes mellitus have high amounts of $HbA_{1c}$ indicating poor control of blood glucose. The International Diabetes Federation and American College of Endocrinology recommend $HbA_{1c}$ values below 48 mmol/mol (6.5%), while the American Diabetes Association recommends that the $HbA_{1c}$ be below 53 mmol/mol (7.0%) for most patients. It has been discovered that Carvedilol can improve insulin receptor sensitivity such that a diabetic patient's $HbA_{1c}$ level reaches and is maintained at or near 7%.

The ability of Carvedilol to improve insulin receptor sensitivity provides a novel means of treating patients with diabetes. Physicians can use Carvedilol to enhance a diabetic patient's natural ability to respond to rising levels of blood glucose. This can reduce the need for other treatments, enhance the effectiveness of other treatments (especially peripherally administered insulin), and delay or prevent progression of the disease. Carvedilol can even improve insulin receptor sensitivity to the extent that no other treatment of the diabetes is needed.

By reducing or eliminating the need for insulin or other treatments, the present invention can minimize the costs and difficulties of conventional treatments of diabetes. By increasing insulin receptor sensitivity, the present invention may reduce or eliminate the hyperglycemia and/or hypoglycemia associated with conventional methods of treatment of diabetes mellitus. The present invention may also reduce or eliminate some, if not all, of the long-term vascular complications of diabetes such as coronary disease, heart attack, stroke, heart failure, kidney failure, blindness, erectile dysfunction, neuropathy (loss of sensation, especially in the feet), gangrene, and gastroparesis (slowed emptying of the stomach). Additionally, the present invention may reduce or eliminate the hyperinsulinemia associated with the peripheral administration (e.g., subcutaneous, intrapulmonary, intranasal, buccal mucosal) of insulin.

Various objects, features, aspects, and advantages of the present invention will become more apparent from the following detailed description of preferred embodiments of the invention

DETAILED DESCRIPTION OF PREFERRED EMBODIMENTS

Before various embodiments of the present invention are explained in detail, it is to be understood that the invention is not limited in its application to the methods set forth in the following description. The invention is capable of other embodiments and of being practiced or of being carried out in various ways. These embodiments are simply illustrative, and only the claims are meant to define the scope of the invention.

In one embodiment of the present invention, an administering physician prescribes Carvedilol to a patient under a ramping up period until the patient reaches an effective amount. The initial dosage is 6.25 mg administered twice daily. That amount will double after the first week and double again every-other week until the patient's HbA1c level maintains within a healthy range. The patient will then continue taking that effective dose. The effective amount of Carvedilol is preferably between 25 mg given twice daily and 50 mg given twice daily, but can be dependent upon a patient's body weight. For example, most patients weighing in excess of 85 kg require 50 mg Carvedilol twice daily while most patients weighing less than 85 kg only require 25 mg Carvedilol twice daily. When the dosage of Carvedilol is too low, $HbA_{1c}$ levels do not fall within the normal range of 7.0% or lower. When the dosage is too high, side effects of the drug can become more prevalent. The physician will require quarterly visits to monitor the patient's success.

In another embodiment, the present invention provides a method for replacing insulin and other blood sugar controlling agents in patients with Type II diabetes mellitus. Carvedilol is administered at first in combination with the patient's existing diabetic medications. As blood glucose and $HbA_{1c}$ levels decrease to normal ranges, the patient will discontinue the use of peripherally administered insulin and other anti-diabetic medications. Eventually, within four to six weeks, and preferably within two to three weeks, the patient will continue taking an effective amount of Carvedilol alone in the absence of the previously required peripherally administered insulin. The effective amount will be sufficient to increase insulin receptor sensitivity such that the patient's body will be able to naturally maintain glucose homeostasis.

In another embodiment, the present invention provides a method for reducing the insulin needs of patients with Type I diabetes mellitus. Carvedilol is administered at first in combination with the patient's insulin. The increased insulin receptor sensitivity will naturally lower blood glucose and $HbA_{1c}$ levels. Since the insulin receptor is regaining its sensitivity, the response to peripherally administered insulin will correspondingly increase such that lower dosages of insulin will yield better results. The patient will also be able to discontinue use of other anti-diabetic medications, if taking any. Eventually, likely within four to six weeks, and preferably within two to three weeks, the patient will continue taking an effective amount of Carvedilol in conjunction with a now-lessened requirement of peripherally administered insulin. The effective amount of Carvedilol will be sufficient to increase insulin receptor sensitivity such that the patient's body will require less peripherally administered insulin to be able to maintain glucose homeostasis indefinitely. Due to the nature of the disease, patients who suffer from Type I diabetes mellitus will never be able to fully withdraw from peripherally administered insulin, but the present invention will allow said patients to dramatically decrease their peripherally administered insulin requirements.

In another embodiment, the present invention provides a method for delaying and/or preventing the progression of non-insulin dependent Type II diabetes mellitus to insulin-dependent Type II diabetes mellitus. Patients in early stages of Type II diabetes mellitus are able to regulate their blood sugar without the use of insulin (through diet, exercise, anti-diabetic medications, or some combination thereof). These patients are able to use an effective amount of Carvedilol to improve the insulin receptor sensitivity. In doing so, they are able to continue managing their blood sugar without peripherally administered insulin for longer, or indefinitely. As in the methods above, the result is achieved by administering Carvedilol, at first in combination with the patient's existing diabetic medications. As blood glucose and $HbA_{1c}$ levels decrease the patient will discontinue the use of other anti-diabetic medications. Eventually, likely within four to six weeks, and preferably within two to three weeks, the patient will continue taking an effective amount of Carvedilol. The effective amount will be sufficient to increase insulin receptor sensitivity such that the patient's body will be able to naturally maintain glucose homeostasis.

According to other embodiments of the present invention, administration of an effective amount of Carvedilol controls a rise in glucose typically associated with ingesting a meal (i.e., the post-prandial rise in glucose). The post-prandial rise in glucose may be partially or completely controlled by methods of the present invention since insulin receptor function is improved such that the body will naturally release insulin to combat rising levels of blood glucose.

According to embodiments of the present invention, Carvedilol is preferably administered at appropriate dosages and frequencies so as to achieve and/or maintain homeostatic function of the insulin receptor such that it maintains glucose homeostasis in patients with Type II diabetes mellitus. Carvedilol is also preferably administered at appropriate dosages and frequencies so as to improve function of the insulin receptor such that it helps maintain glucose homeostasis with limited dosages of peripherally administered insulin in patients with Type I diabetes mellitus.

In other embodiments according to the present invention, methods of treating diabetes mellitus in a patient in need thereof comprise orally administering an effective amount of Carvedilol to the patient as described in the various embodiments above and peripherally administering an effective amount of an insulin drug to the patient. The use of peripherally administered insulin is only required in patients with Type I diabetes mellitus since Carvedilol alone can eradicate the need for peripherally administered insulin in patients with Type II diabetes mellitus; as aforementioned. In patients with Type I diabetes mellitus the preferred method of administration of insulin is performed by subcutaneous insulin injection as will be understood by those skilled in the art. It is also known, however, that an oral insulin pill could be developed and administered in lieu of a subcutaneous injection, still in combination with an effective amount of Carvedilol without departing from the scope and spirit of the present invention.

While it has been described to use an oral medication, it should be apparent to those skilled in the art that the use of Carvedilol in other forms is within the scope of this invention. Likewise, it should be known to those skilled in the art to use the active ingredient, Carvedilol, in combination with other inactive ingredients to alleviate or combat the various side effects (skin rash, itching, wheezing, swelling and weight gain, difficulty breathing, chest pain, dizziness, sweating, confusion, etc.) of Carvedilol. It should also be readily apparent to those skilled in the art that the active ingredient, Carvedilol, may be used in either a short- or long-acting capsule to achieve the same results without departing from the spirit of this invention. For example, it is has been described to orally administer two pills per day to achieve the effective amount of Carvedilol in a patient's bloodstream. It is also known to utilize a long-acting version of Carvedilol whereby a single oral administration can result in the same effective amount of Carvedilol as two short-acting pills since the dosage will be equivalent, but will be slowly released into the body throughout a known period of time. All means of delivering Carvedilol are contemplated.

EXAMPLES

Data has been collected utilizing the various methods described herein and included for purposes of showing results and further exemplifying the preferred embodiments of this invention. A study was performed on two groups: Group 1 and Group 2. Both groups included patients with diabetes mellitus and a history of uncontrolled blood sugar. The patients of each group were between the ages of 40 and 85 and consisted of both males and females and various ethnicities. Group 1 consisted of patients that were already on insulin (humulin mix, novolog mix, etc.) and who were unable to control their blood sugar. The patients in Group 2 were taking oral medications, were unable to control their blood sugar, and needed insulin to regulate their disease.

Normal blood sugar levels were considered to be 120 mg % (mg % is milligram per 100 cc blood), which was equivalent to 6.0 $HbA_{1c}$ before meals or while fasting. After the first visit and examination, the patients' blood sugar and $HbA_{1c}$ levels were reviewed. The patients were prescribed Carvedilol and advised on a diet routine as suggested by the American Diabetes Association. Then patients were requested to report their blood sugar weekly. Eventually, as their blood sugar was controlled, patients were taken off insulin completely. $HbA_{1c}$ levels were checked approximately 2-3 months after controlling the blood sugar.

Group 1

Group 1 data is presented below for patients with Type II diabetes mellitus who were already taking insulin and were unable to control their blood sugar. The data includes blood sugar and $HbA_{1c}$ levels before and after taking Carvedilol.

1. JBM-65-M was first seen in January 2012. His $HbA_{1c}$ was more than 9.0 and fasting plasma glucose was 282 mg %. He was taking 35 units at night of Lente insulin and regular insulin before each meal at a dosage of 10-30 units, on a sliding scale. He began taking an effective dosage of Carvedilol with a diet in February 2012. The patient was taken off insulin completely by April 2012; his $HbA_{1c}$ came down to 5.5 and fasting plasma glucose was 122 mg %.
2. BS-81-F was taking 36 units of Humulin N twice a day in February 2012. Her $HbA_{1c}$ was 7.6 and mean plasma glucose was 171 mg %. She began taking an effective dosage of Carvedilol immediately. In April 2012 her $HbA_{1c}$ was 6.5 and her mean plasma glucose was 140 mg %. The patient had been taken off of insulin completely by this time.
3. BD-63-M is a Type I diabetic with two episodes of myocardial infarction and four stents post Percutaneous Transluminal Coronary Angioplasty (PTCA). In January 2012 his $HbA_{1c}$ was 8.2 with a mean plamsa glucose of 203 mg %. He was taking 400 units of Novolog mix 70/30 in two divided doses. After Carvedilol and an improved diet, the dose of insulin has been reduced to a total of 90 units a day in two divided doses. His $HbA_{1c}$ is the same but recent blood sugar was 134 mg %.
4. MO-55-M was first seen in December 2011 with an $HbA_{1c}$ of 11.4 and mean plasma blood glucose of 280 mg %. He was taking Novolog 70/30 40 units twice a day. He was started on Carvedilol with an improved diet. The patient came off of insulin and subsequently reported an $HbA_{1c}$ of 8.6 with a plasma blood glucose of 200 mg % in April 2012. Currently he is reporting a plasma blood glucose below 120 mg %.
5. DK-51-F suffered from renal failure and had an $HbA_{1c}$ of 10.3 and mean plasma glucose of 249 mg % when first seen. She was taking Novlog mix 70/30 20 units twice a day. After five weeks on Carvedilol, she was taken off insulin and reported a plasma glucose of less than 120 mg %, which corresponds to an $HbA_{1c}$ of 6.0.

Group 2

Group 2 consisted of Type II diabetes mellitus patients who could not control their blood sugar on diet nor oral medication and would need to start insulin. Carvedilol was used in place of insulin to control blood sugar as well as other anti-diabetic oral medications.

1. AA-70-M had a blood sugar of 200 mg % and was intolerant to all oral anti-diabetics except Sitagliptin. Sitagliptin did not fully control his blood sugar, therefore Carvedilol was prescribed. Taking both of these medications resulted in the patient experiencing hypoglycemia. Sitagliptin was then discontinued and the hypoglycemia subsequently disappeared. Carvedilol has controlled the patient's blood sugar. The last recorded $HbA_{1c}$ was 6.8

2. LF-54-M had poorly controlled blood sugar but managed an $HbA_{1c}$ of 8.0 and mean fasting glucose of 183 mg %. She was taking three oral medications: Metformin 1000 mg BID, Sitagliptin 100 mg daily and Sulfonylurea. She was started on Carvedilol and her blood sugar came down to 90 mg %. She then discontinued use of Sitagliptin. Her $HbA_{1c}$ level is 6.5

3. HA-46-F had an $HbA_{1c}$ of 8.5 and fasting plasma glucose of 197 mg %. She was prescribed Metformin and Glyburide Micro. She was also given Bayetta, however her blood sugar remained uncontrolled. She started on Carvedilol recently and her blood sugar has reached normal levels. Her $HbA_{1c}$ level is 8.4

4. JF-65-F had a long standing history of poorly controlled blood sugar due to serious non-compliance. The patient also suffered from severe Peripheral Neuritis. Her $HbA_{1c}$ was 10.2 in December 2011. The patient was taking Metformin 1000 mg twice a day, Sitagliptin 100 mg daily and Glyburide Micro 6 mg twice a day. The patient was started on Carvedilol in February 2012. Her $HbA_{1c}$ in late March 2012 was down to 8.2 with a mean plasma glucose of 189 mg %. More recently she has reported blood sugar of 95 mg % and stopped taking Glyburide Micro. Her $HbA_{1c}$ is now 7.8.

5. FL-76-M had an $HbA_{1c}$ of 8.3 and mean plasma gluclose of 163 mg %. He has been on Janumet 50/10 twice a day, Glymeperide which was changed to Glyburide Micro 3 mg twice daily. He had a shot of cortisone in his right knee which caused his blood sugar to rise to 273 mg %. Carvedilol was added to his regimen and his blood sugar was recently reported at 81 mg %. The patient was able to stop Glyburide Micro. His $HbA_{1c}$ level is 7.1

Thus, several illustrative embodiments have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A method of treating Type I diabetes mellitus in a patient comprising administering an amount of Carvedilol to the patient to improve insulin receptor sensitivity, wherein said amount is sufficient to delay or prevent the progression of Type I diabetes mellitus.

2. The method of claim 1 wherein the amount of Carvedilol administered is sufficient to reduce the need for other treatments of Type I diabetes mellitus.

3. The method of claim 1 wherein the amount of Carvedilol administered is sufficient to reduce the patient's need for peripherally administered insulin.

4. The method of claim 1 wherein the amount of Carvedilol administered is sufficient to enhance the effectiveness of peripherally administered insulin.

5. The method of claim 3 wherein the amount of Carvedilol administered is an amount sufficient to reach and maintain healthy blood glucose control.

6. The method of claim 3 wherein the amount of Carvedilol administered is an amount sufficient to reach and maintain HbA1c levels near 7% or less.

7. The method of claim 3 wherein insulin receptor sensitivity is improved sufficiently to reduce the need for other treatments of the Type I diabetes mellitus.

8. The method of claim 3 wherein insulin receptor sensitivity is improved sufficiently to enhance the effectiveness of peripherally administered insulin.

9. A method of treating diabetes mellitus in a patient being administered an amount of peripherally administered insulin comprising:
   administering a starting dosage of Carvedilol to a patient;
   continuing to administer Carvedilol, while increasing the amount administered until it is sufficient to improve insulin receptor sensitivity in the patient; and
   reducing or eliminating the amount of peripherally administered insulin.

10. The method of claim 9 wherein the amount of Carvedilol administered is sufficient to improve insulin receptor sensitivity in the patient when the patient reaches and maintains HbA1c levels near 7%.

11. The method of claim 9 further comprising reducing or eliminating the use of other treatments of diabetes mellitus.

12. A method of treating Type II diabetes mellitus in a patient comprising administering an amount of Carvedilol to the patient to improve insulin receptor sensitivity, wherein said amount is sufficient to delay or prevent the progression of non-insulin dependent Type II diabetes mellitus to insulin dependent Type II diabetes mellitus.

13. The method of claim 12 wherein said amount is sufficient to allow reduction or discontinuation of the use of peripherally administered insulin for the treatment of said patient.

14. The method of claim 13 wherein insulin receptor sensitivity is improved sufficiently to allow the patient's body to manage the post-prandial rise in blood glucose without administering insulin.

15. The method of claim 12 wherein the amount of Carvedilol administered is sufficient to reduce the need for other treatments of the Type II diabetes mellitus.

16. The method of claim 12 wherein the amount of Carvedilol administered is sufficient to enhance the effectiveness of peripherally administered insulin.

17. The method of claim 12 wherein the amount of Carvedilol administered is an amount sufficient to reach and maintain healthy blood glucose control.

18. The method of claim 12 wherein the amount of Carvedilol administered is an amount sufficient to reach and maintain HbA1c levels near 7% or less.

* * * * *